(12) United States Patent
Spier et al.

(10) Patent No.: US 6,825,010 B2
(45) Date of Patent: Nov. 30, 2004

(54) METHODS AND COMPOSITIONS FOR NUCLEOTIDE ANALYSIS

(75) Inventors: Eugene Spier, Palo Alto, CA (US); Victoria L. Boyd, San Carlos, CA (US)

(73) Assignee: Applera Corporation, Foster City, CA (US)

(*) Notice: Subject to any disclaimer, the term of this patent is extended or adjusted under 35 U.S.C. 154(b) by 130 days.

(21) Appl. No.: 10/124,038

(22) Filed: Apr. 16, 2002

(65) Prior Publication Data

US 2003/0082572 A1 May 1, 2003

Related U.S. Application Data

(60) Provisional application No. 60/284,409, filed on Apr. 16, 2001.

(51) Int. Cl.[7] ............................ C12P 19/34; C12Q 1/68; C07H 21/04
(52) U.S. Cl. .................... 435/91.2; 435/6; 435/91.1; 536/23.1; 536/24.3; 536/24.33
(58) Field of Search .......................... 435/6, 91.1, 91.2; 536/23.1, 24.3, 24.33, 24.2; 204/450; 356/344

(56) References Cited

U.S. PATENT DOCUMENTS 5,185,243 A   2/1993  Ullman et al.
6,045,994 A   4/2000  Zabeau et al.
6,197,557 B1  3/2001  Makarov et al.

FOREIGN PATENT DOCUMENTS

EP   0 534 858 A1    3/1993
WO   WO 00/61801     10/2000

OTHER PUBLICATIONS

Blears et al., "Amplified fragment length polymorphism (AFLP): a review of the procedure and its application," Journal of Industrial Microbiology & Biotechnology, 1998, vol. 21, pp. 99–114.*

International Search Report for PCT Application No. PCT/US02/11931, mailed Sep. 11, 2002.

* cited by examiner

*Primary Examiner*—Kenneth R. Horlick
*Assistant Examiner*—Young J. Kim
(74) *Attorney, Agent, or Firm*—Finnegan, Henderson, Farabow, Garrett & Dunner, L.L.P.

(57) ABSTRACT

The invention relates generally to the field of nucleic acid sequence analysis. In certain embodiments, the analysis is genotyping. In certain embodiments, the analysis involves detecting single nucleotide polymorphisms (SNPs). The invention also relates to methods, kits, and computer software for nucleic acid analysis.

11 Claims, 10 Drawing Sheets

Estimated Genomic AFLP and Number of SNPs Between BstYI & MseI

| Selective BstYI-MseI +3 bin | #SNPs in the "bin" | #AFLP fragments |
|---|---|---|
| CAA_AAA | 796 | 7969 |
| CAA_AAC | 265 | 2697 |
| CAA_AAG | 364 | 3387 |
| CAA_AAT | 486 | 5599 |
| CAA_ACA | 245 | 2365 |
| CAA_ACC | 170 | 1494 |
| CAA_ACG | 23 | 272 |
| CAA_ACT | 232 | 2184 |
| CAA_AGA | 263 | 2882 |
| CAA_AGC | 176 | 1696 |
| CAA_AGG | 199 | 1884 |
| CAA_AGT | 234 | 2697 |
| CAA_ATA | 341 | 3708 |
| CAA_ATC | 187 | 2011 |
| CAA_ATG | 289 | 3220 |
| ... | ... | ... |
| TTT_GTT | 169 | 2234 |
| TTT_TAA | 365 | 4914 |
| TTT_TAC | 164 | 1861 |
| TTT_TAG | 155 | 2302 |
| TTT_TAT | 339 | 3907 |
| TTT_TCA | 199 | 2715 |
| TTT_TCC | 160 | 1724 |
| TTT_TCG | 18 | 202 |
| TTT_TCT | 232 | 2598 |
| TTT_TGA | 298 | 3365 |
| TTT_TGC | 125 | 1678 |
| TTT_TGG | 198 | 2079 |
| TTT_TGT | 250 | 2856 |
| TTT_TTA | 209 | 2439 |
| TTT_TTC | 255 | 2748 |
| TTT_TTG | 190 | 2315 |
| TTT_TTT | 489 | 5365 |
| Total | 336282 | 3483954 |

Estimated AFLP of the Human Genome: ~3.5 Million BstYI-MseI Fragments that Collectively Contain Over 300,000 SNPs

FIG. 3

SEQUENCE LISTING

<160> NUMBER OF SEQ ID NOS: 49

<210> SEQ ID NO 1
<211> LENGTH: 21
<212> TYPE: DNA
<213> ORGANISM: Artificial Sequence
<220> FEATURE:
<223> OTHER INFORMATION: Description: synthesized oligonucleotide primer

<400> SEQUENCE: 1
gcgacgatga gtcctgagta a                    21

<210> SEQ ID NO 2
<211> LENGTH: 21

```
<212> TYPE: DNA
<213> ORGANISM: Artificial Sequence
<220> FEATURE:
<223> OTHER INFORMATION: Description: synthesized oligonucleotide primer

<400> SEQUENCE: 2
ctcgtagact gcgtaccgat c                                                 21

<210> SEQ ID NO 3
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 3
gcgacgatga gtcctgagta aag                                               23

<210> SEQ ID NO 4
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 4
gcgacgatga gtcctgagta aca                                               23

<210> SEQ ID NO 5
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 5
gcgacgatga gtcctgagta agg                                               23

<210> SEQ ID NO 6
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 6
gcgacgatga gtcctgagta agt                                               23

<210> SEQ ID NO 7
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 7
gcgacgatga gtcctgagta ata                                               23

<210> SEQ ID NO 8
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 8
```

```
gcgacgatga gtcctgagta atc                                              23
```

<210> SEQ ID NO 9
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 9

```
gcgacgatga gtcctgagta atg                                              23
```

<210> SEQ ID NO 10
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 10

```
gcgacgatga gtcctgagta att                                              23
```

<210> SEQ ID NO 11
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 11

```
ctcgtagact gcgtaccgat cca                                              23
```

<210> SEQ ID NO 12
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 12

```
ctcgtagact gcgtaccgat ccc                                              23
```

<210> SEQ ID NO 13
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 13

```
ctcgtagact gcgtaccgat cct                                              23
```

<210> SEQ ID NO 14
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 14

```
ctcgtagact gcgtaccgat ctc                                              23
```

<210> SEQ ID NO 15
<211> LENGTH: 23
<212> TYPE: DNA
<213> ORGANISM: Artificial Sequence

```
-continued

<220> FEATURE:
<223> OTHER INFORMATION: Description: synthesized oligonucleotide primer

<400> SEQUENCE: 15
ctcgtagact gcgtaccgat ctt                                              23

<210> SEQ ID NO 16
<211> LENGTH: 24
<212> TYPE: DNA
<213> ORGANISM: Artificial Sequence
<220> FEATURE:
<223> OTHER INFORMATION: Description: synthesized oligonucleotide primer

<400> SEQUENCE: 16
gcgacgatga gtcctgagta aaaa                                             24

<210> SEQ ID NO 17
<211> LENGTH: 24
<212> TYPE: DNA
<213> ORGANISM: Artificial Sequence
<220> FEATURE:
<223> OTHER INFORMATION: Description: synthesized oligonucleotide primer

<400> SEQUENCE: 17
ctcgtagact gcgtaccgat cctt                                             24

<210> SEQ ID NO 18
<211> LENGTH: 19
<212> TYPE: DNA
<213> ORGANISM: Artificial Sequence
<220> FEATURE:
<223> OTHER INFORMATION: Description: synthesized oligonucleotide primer

<400> SEQUENCE: 18
actgttggac acacaggag                                                   19

<210> SEQ ID NO 19
<211> LENGTH: 21
<212> TYPE: DNA
<213> ORGANISM: Artificial Sequence
<220> FEATURE:
<223> OTHER INFORMATION: Description: synthesized oligonucleotide primer

<400> SEQUENCE: 19
gcactgttgg acacacagga g                                                21

<210> SEQ ID NO 20
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 20
ctgtctcatt cttgggtttt cct                                              23

<210> SEQ ID NO 21
<211> LENGTH: 27
<212> TYPE: DNA
<213> ORGANISM: Artificial Sequence
<220> FEATURE:
<223> OTHER INFORMATION: Description: synthesized oligonucleotide primer

<400> SEQUENCE: 21
ttttgtagct catggtggaa caaatgg                                          27
```

```
<210> SEQ ID NO 22
<211> LENGTH: 31
<212> TYPE: DNA
<213> ORGANISM: Artificial Sequence
<220> FEATURE:
<223> OTHER INFORMATION: Description: synthesized oligonucleotide primer

<400> SEQUENCE: 22
ttttttttct ctgaagattt attagacgtt g                              31

<210> SEQ ID NO 23
<211> LENGTH: 35
<212> TYPE: DNA
<213> ORGANISM: Artificial Sequence
<220> FEATURE:
<223> OTHER INFORMATION: Description: synthesized oligonucleotide primer

<400> SEQUENCE: 23
tttttttttt ttggtatccc ttcggaagtt gcctg                          35

<210> SEQ ID NO 24
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 24
gaattgttct ataagggcat ccg                                       23

<210> SEQ ID NO 25
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 25
cctgacccct ctccttcata aat                                       23

<210> SEQ ID NO 26
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 26
ctgtctcatt cttgggtttt cct                                       23

<210> SEQ ID NO 27
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 27
agaatgacct tcttggtcat cca                                       23

<210> SEQ ID NO 28
<211> LENGTH: 23
<212> TYPE: DNA
<213> ORGANISM: Artificial Sequence
<220> FEATURE:
<223> OTHER INFORMATION: Description: synthesized oligonucleotide primer
```

```
<400> SEQUENCE: 28
ctctgaagat ttattagacg ttg                                              23

<210> SEQ ID NO 29
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 29
ggtatccctt cggaagttgc ctg                                              23

<210> SEQ ID NO 30
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 30
catgggtata tagccatgtc cct                                              23

<210> SEQ ID NO 31
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 31
gcccttgcta cactggcact cac                                              23

<210> SEQ ID NO 32
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 32
taactacaag ggacaggtgc tga                                              23

<210> SEQ ID NO 33
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 33
catgaggaca aatatcattc tga                                              23

<210> SEQ ID NO 34
<211> LENGTH: 22
<212> TYPE: DNA
<213> ORGANISM: Artificial Sequence
<220> FEATURE:
<223> OTHER INFORMATION: Description: synthesized oligonucleotide primer

<400> SEQUENCE: 34
ctcgtagact gcgtaccgat ct                                               22

<210> SEQ ID NO 35
```

-continued

```
<211> LENGTH: 22
<212> TYPE: DNA
<213> ORGANISM: Artificial Sequence
<220> FEATURE:
<223> OTHER INFORMATION: Description: synthesized oligonucleotide primer

<400> SEQUENCE: 35
gcgacgatga gtcctgagta at                                              22

<210> SEQ ID NO 36
<211> LENGTH: 22
<212> TYPE: DNA
<213> ORGANISM: Artificial Sequence
<220> FEATURE:
<223> OTHER INFORMATION: Description: synthesized oligonucleotide primer

<400> SEQUENCE: 36
ctcgtagact gcgtaccgat cc                                              22

<210> SEQ ID NO 37
<211> LENGTH: 22
<212> TYPE: DNA
<213> ORGANISM: Artificial Sequence
<220> FEATURE:
<223> OTHER INFORMATION: Description: synthesized oligonucleotide primer

<400> SEQUENCE: 37
gcgacgatga gtcctgagta aa                                              22

<210> SEQ ID NO 38
<211> LENGTH: 22
<212> TYPE: DNA
<213> ORGANISM: Artificial Sequence
<220> FEATURE:
<223> OTHER INFORMATION: Description: synthesized oligonucleotide primer

<400> SEQUENCE: 38
gcgacgatga gtcctgagta ac                                              22

<210> SEQ ID NO 39
<211> LENGTH: 22
<212> TYPE: DNA
<213> ORGANISM: Artificial Sequence
<220> FEATURE:
<223> OTHER INFORMATION: Description: synthesized oligonucleotide primer

<400> SEQUENCE: 39
gcgacgatga gtcctgagta ag                                              22

<210> SEQ ID NO 40
<211> LENGTH: 17
<212> TYPE: DNA
<213> ORGANISM: Artificial Sequence
<220> FEATURE:
<223> OTHER INFORMATION: Description: synthesized oligonucleotide primer

<400> SEQUENCE: 40
acatcctttc cagcatc                                                    17

<210> SEQ ID NO 41
<211> LENGTH: 17
<212> TYPE: DNA
<213> ORGANISM: Artificial Sequence
<220> FEATURE:
<223> OTHER INFORMATION: Description: synthesized oligonucleotide primer

<400> SEQUENCE: 41
```

```
tcagtctcca catttgc                                                  17

<210> SEQ ID NO 42
<211> LENGTH: 16
<212> TYPE: DNA
<213> ORGANISM: Artificial Sequence
<220> FEATURE:
<223> OTHER INFORMATION: Description: synthesized oligonucleotide primer

<400> SEQUENCE: 42
tacactccca ccaaca                                                   16

<210> SEQ ID NO 43
<211> LENGTH: 18
<212> TYPE: DNA
<213> ORGANISM: Artificial Sequence
<220> FEATURE:
<223> OTHER INFORMATION: Description: synthesized oligonucleotide primer

<400> SEQUENCE: 43
cctgcagatt ttgattcg                                                 18

<210> SEQ ID NO 44
<211> LENGTH: 16
<212> TYPE: DNA
<213> ORGANISM: Artificial Sequence
<220> FEATURE:
<223> OTHER INFORMATION: Description: synthesized oligonucleotide primer

<400> SEQUENCE: 44
gtgttagcca ggatgg                                                   16

<210> SEQ ID NO 45
<211> LENGTH: 23
<212> TYPE: DNA
<213> ORGANISM: Artificial Sequence
<220> FEATURE:
<223> OTHER INFORMATION: Description: synthesized oligonucleotide primer

<400> SEQUENCE: 45
gtgcttctaa gtatatgtgt act                                           23

<210> SEQ ID NO 46
<211> LENGTH: 18
<212> TYPE: DNA
<213> ORGANISM: Artificial Sequence
<220> FEATURE:
<223> OTHER INFORMATION: Description: synthesized oligonucleotide primer

<400> SEQUENCE: 46
gggagggagg tattctag                                                 18

<210> SEQ ID NO 47
<211> LENGTH: 20
<212> TYPE: DNA
<213> ORGANISM: Artificial Sequence
<220> FEATURE:
<223> OTHER INFORMATION: Description: synthesized oligonucleotide primer

<400> SEQUENCE: 47
tcatcagaat gacttagcag                                               20

<210> SEQ ID NO 48
<211> LENGTH: 22
<212> TYPE: DNA
```

```
<213> ORGANISM: Artificial Sequence
<220> FEATURE:
<223> OTHER INFORMATION: Description: synthesized oligonucleotide primer

<400> SEQUENCE: 48
ctgagatttg atctcttctt ca                                              22

<210> SEQ ID NO 49
<211> LENGTH: 18
<212> TYPE: DNA
<213> ORGANISM: Artificial Sequence
<220> FEATURE:
<223> OTHER INFORMATION: Description: synthesized oligonucleotide primer

<400> SEQUENCE: 49
atgcaagaaa ccttcagg                                                   18
```

METHODS AND COMPOSITIONS FOR NUCLEOTIDE ANALYSIS

This application claims priority of U.S. Provisional Application No. 60/284,409, filed Apr. 16, 2001, which is hereby incorporated by reference herein in its entirety for any purpose.

FIELD OF THE INVENTION

The invention relates generally to the field of nucleic acid sequence analysis. In certain embodiments, the analysis is genotyping. In certain embodiments, the analysis involves detecting single nucleotide polymorphisms (SNPs). The invention also relates to methods, kits, and computer software for nucleic acid analysis.

BACKGROUND OF THE INVENTION

There are various methods for nucleic acid analysis. One method involves the use of restriction fragment length polymorphisms (RFLPs). Another method uses amplified fragment length polymorphisms (AFLPs).

Analysis of allelic differences between individuals is one area of nucleic acid analysis. In certain applications, one detects single nucleotide polymorphisms (SNPs). Approximately $2.9 \times 10^6$ SNPs have been mapped and sequenced in the human genome, which covers approximately $3 \times 10^9$ base pairs. Effective analysis of an individual's genome on efficient and rapid scale would be very beneficial.

SUMMARY OF THE INVENTION

In certain embodiments, a method of nucleic acid analysis is provided. Certain such embodiments comprise generating multiple fragments of nucleic acid target sequence by digesting the target sequence with at least one restriction enzyme, and amplifying the multiple fragments employing a first set of primers to generate multiple amplified fragments.

According to certain embodiments, the method further comprises detecting a nucleotide for at least one of the amplified subsets of the multiple amplified fragments. According to certain embodiments, the amplifying includes using a second set of primers, which include at least one additional nucleotide on the 3' ends of the first set of primers, to amplify a subset of the multiple amplified fragments to generate an amplified subset of the multiple amplified fragments.

In certain embodiments, the amplifying involves the use of one or more subsequent sets of primers, which include at least one additional nucleotide on the 3' ends of the first set of primers, to sequentially create one or more subsets of amplified fragments.

In certain embodiments, the amplified subset of the multiple amplified fragments are asymmetrically amplified to generate single-stranded DNA prior to the detecting a nucleotide for at least one of the amplified subsets of the multiple amplified fragments.

According to certain embodiments, methods of performing single base extension reactions isothermally are provided.

According to certain embodiments, single stranded template is prepared for use in single base extension reactions. In certain embodiments, the single stranded template is prepared by asymmetric PCR.

According to certain embodiments, further amplification is performed with one primer from the first primer pair, and at least one primer which comprises a sequence corresponding to an area immediately adjacent to a nucleotide to be detected. According to certain embodiments, an excess of the primer from the first primer pair is added to generate a long oligonucleotide primer of a known length, wherein the 3' end of the long primer is proximal to the nucleotide to be detected. In certain of these embodiments, labeled sequence terminators are added to the reaction containers, and a single base extension, or minisequencing, reaction is performed. In certain embodiments, the products of the minisequencing reactions are resolved according to the length of the long oligonucleotide. In certain embodiments, the minisequencing reaction is performed isothermally.

According to certain embodiments of the invention, a kit is provided. In certain embodiments, such a kit comprises a first pair of primers for the amplification of AFLPs. The first pair of primers comprise a first primer and a second primer. Such a kit further comprises a second set of primers, wherein the primers of the second set comprise a sequence identical to the primers used to generate the AFLPs, and further comprise a single nucleotide added to the 3' end of the primer of the first primer set.

According to certain embodiments, software is provided. In certain embodiments this software identifies known SNPs from an electronic database, designs primers comprising sequence of an area immediately adjacent to a known SNP, calculates melting temperatures for the primers, and selects a primer based on the calculated melting temperature.

BRIEF DESCRIPTION OF THE FIGURES

The patent or application file contains at least one drawing executed in color. Copies of this patent or patent application publication with color drawings will be provided by the Office upon request and payment of the necessary fee.

FIG. 3 shows the estimated number of AFLP fragments generated by restriction digestion with Mse I and Bst YI in prospective bins employing 3 additional nucleotides 3' of the amplification primers. The number of known SNPs in each bin are also shown.

DETAILED DESCRIPTION OF CERTAIN EMBODIMENTS OF THE INVENTION

Figure 1:
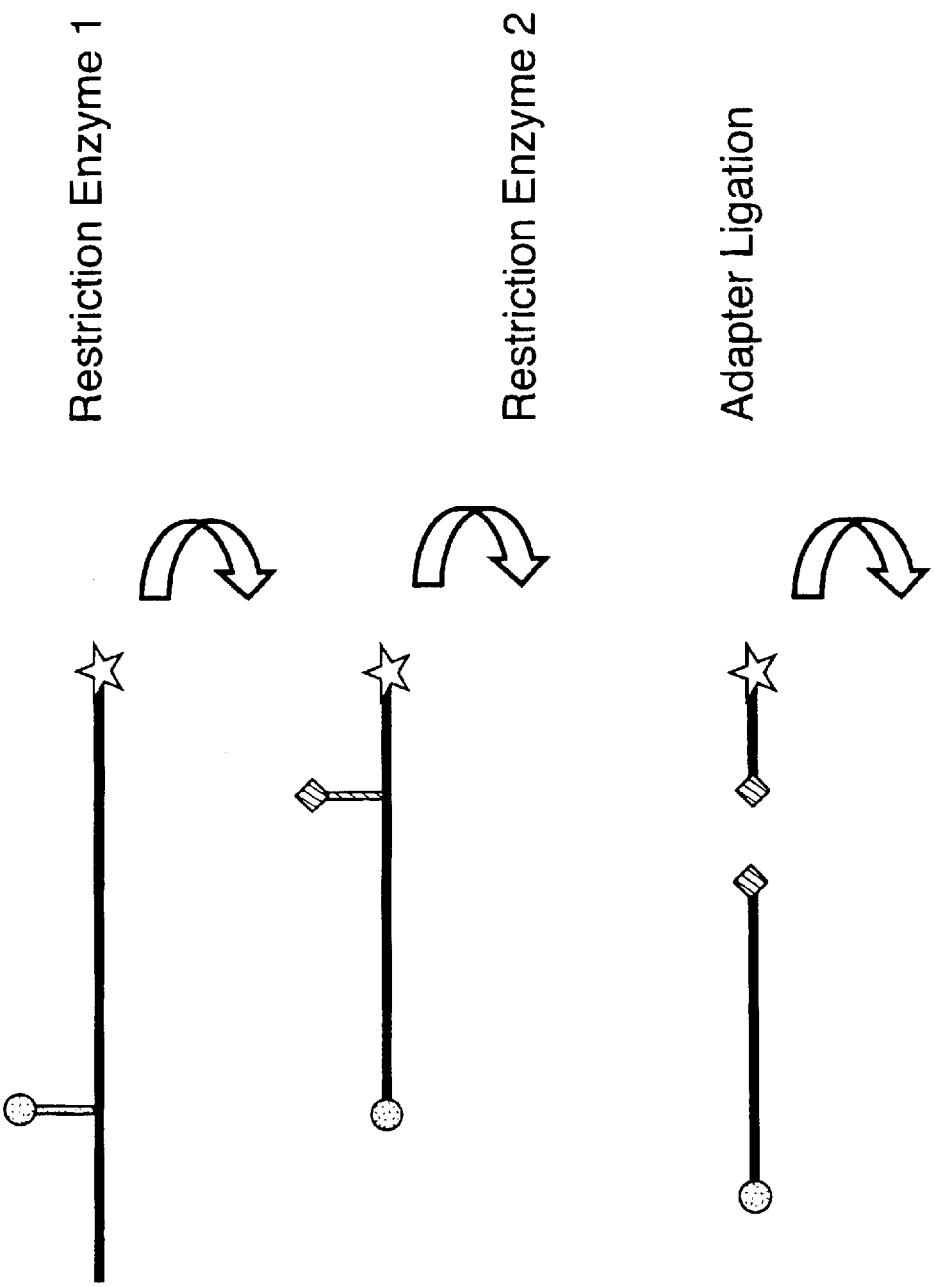
FIG. 1 illustrates fragment generation by restriction enzyme digestion and subsequent ligation of adaptors.

The section headings used herein are for organizational purposes only, and are not to be construed as limiting the subject matter described. All documents cited in this application, including but not limited to patents, patent applications, articles, books, and treatises, are expressly incorporated by reference in their entirety for any purpose.

Definitions

The term "adaptors" refers to an oligonucleotide which is ligated to the end of another polynucleotide through a ligation reaction. Adaptors may be single or double stranded. Typically, an adaptor may add a useful feature to the end of a polynucleotide. Such features may include, but are not limited to, restriction enzyme sites or unique sequences. In certain embodiments, unique sequences may be used as sites for amplification primers specific to the adaptors.

"Isothermal conditions" are a substantially uniform or constant temperature at which the modification or polymerization of a primer oligonucleotide is carried out in accordance with the present invention. The temperature is chosen so that the duplex formed with the primer oligonucleotide and a polynucleotide is near equilibrium with the unhybridized oligonucleotide and unhybridized polynucleotide. The near equilibrium state is that state where oligonucleotides that form a duplex with a polynucleotide can dissociate and become single-stranded again without cycling of temperature. In certain embodiments, at least 1%, in certain embodiments 20 to 80%, and in certain embodiments less than 95% of the polynucleotide is hybridized to the primer oligonucleotide under the isothermal conditions. Accordingly, under isothermal conditions there are polynucleotides that are hybridized with the primer oligonucleotide, or portions thereof, and are in dynamic equilibrium with molecules that are not hybridized with the oligonucleotide. Isothermal conditions may include some fluctuation of the temperature. According to certain embodiments, temperature fluctuations can be ±2° C.

Accordingly, the term "isothermal conditions" includes the use of a fluctuating temperature, for example, particularly random or uncontrolled fluctuations in temperature. The term, hence, excludes the type of fluctuation in temperature referred to as thermal cycling, which is employed in some known amplification procedures, e.g., PCR.

Isothermal conditions include reversibly hybridizing a primer to a target polynucleotide sequence at a temperature between 40° and 80° C. In certain embodiments, the isothermal temperature is arrived at empirically by carrying out the present method at different temperatures and determining the optimum temperature resulting in the amplification best suited to the requirements of the method. Computer models may also be used to select the appropriate temperature. Use of isothermal conditions in polymerization reactions has been described, e.g., in U.S. Pat. No. 5,882,867.

The term "minisequencing" reaction refers to a type of single base extension sequencing reaction using sequence terminators. In certain embodiments, minisequencing reactions are performed in the substantial absence of free single nucleotides, to minimize or prevent polymerization of nucleic acid beyond the single nucleotide sequenced by the sequence terminator. In certain embodiments, sequence terminators are labeled with fluorescent dyes, so that each nucleotide (A, G, T, or C) is identifiable by the color of the fluorescent label. Exemplary sequence terminators and reactions employing them are described, e.g., in U.S. Pat. Nos. 5,498,523; and 4,994,372.

The term "mobility modifiers" refers to agents and chemicals, including but not limited to, nucleic acid, that alter the mobility and migration properties of a nucleic acid. Examples of mobility modifiers have been described, e.g., in U.S. Pat. Nos. 5,703,222; 5,470,705; 5,777,096; 5,514,543; and 5,703,096.

The term "multiplex" refers to multiple reactions occurring in the same reaction container. In certain embodiments, the reactions are performed on or with multiple nucleic acid targets.

The term "single nucleotide polymorphism," or "SNP," refers to a polymorphism or allelic variation at a genetic locus, where the alleles differ by one nucleotide.

The term "unique sequence identifier" refers to an oligonucleotide sequence which is substantially different from other oligonucleotide sequences within a sample. In certain embodiments, a unique sequence identifier preferably demonstrates little or no cross-reactivity with a sample nucleic acid, or other unique sequence identifiers. In certain embodiments, unique sequence identifiers may be attached to an oligonucleotide known to complement a target polynucleotide. In certain embodiments, the unique sequence identifier, and any attached nucleic acids, may be isolated using oligonucleotides complementary to the unique sequence identifier.

In certain embodiments the unique sequence identifier may then used to selectively bind or remove target polynucleotide from a sample. This is accomplished when the resulting nucleic acid duplex can be selectively bound to another selective oligonucleotide complementary to the unique sequence identifier. In certain embodiments, the other selective oligonucleotide may be bound to a substrate to facilitate purification of the target polynucleotide. Such unique sequence identifiers have been described, e.g., in U.S. Pat. No. 5,981,176; and PCT publication WO 97/31256.

The terms "polynucleotide" and "oligonucleotide" mean polymers of nucleotide monomers, including analogs of such polymers, including double and single stranded deoxyribonucleotides, ribonucleotides, α-anomeric forms thereof, and the like. Descriptions of how to synthesize oligonucleotides can be found, among other places, in U.S. Pat. Nos. 4,373,071; 4,401,796; 4,415,732; 4,458,066; 4,500,707; 4,668,777; 4,973,679; 5,047,524; 5,132,418; 5,153,319; and 5,262,530. Polynucleotides and oligonucleotides can be of any length.

"Primers" are oligonucleotides that comprise sequences that are employed in a reaction to facilitate polymerization of the primer and at least one additional nucleotide. Polymerization may be carried out for purposes of amplification, primer extension, and/or sequencing. Primers according to the present invention refer to oligonucleotides that are designed to hybridize with a portion of the target polynucleotide or amplification products in a sequence-specific manner, and serve as primers for primer extension, amplification and/or sequencing reactions.

The criteria for designing sequence-specific primers are well known to persons of skill in the art. Detailed descriptions of primer design that provide for sequence-specific annealing can be found, among other places, in Diffenbach and Dveksler, PCR Primer, A Laboratory Manual, Cold Spring Harbor Press, 1995, and Kwok et al. (Nucl. Acid Res. 18:999–1005, 1990). The sequence-specific portions of the primers are of sufficient length to permit specific annealing to complementary sequences in ligation products and amplification products, as appropriate.

Many types of amplification may be used for various embodiments of the invention. Exemplary amplification methods include, but are not limited to, PCR, the ligase chain reaction (LCR), Q-beta replicase-based systems, NASBA, 3SR, and rolling circle replication. In certain embodiments, PCR is the amplification method used.

Methods of optimizing amplification reactions are well known to those skilled in the art. For example, it is well known that PCR may be optimized by altering times and temperatures for annealing, polymerization, and denaturing, as well as changing the buffers, salts, and other reagents in the reaction composition. Optimization can also be affected by the design of the amplification primers used. For example, the length of the primers, as well as the G-C:A-T ratio can alter the efficiency of primer annealing, thus altering the amplification reaction. See James G. Wetmur, "Nucleic Acid Hybrids, Formation and Structure," in Molecular Biology and Biotechnology, pp.605–8, (Robert A. Meyers ed., 1995).

Figure 2:
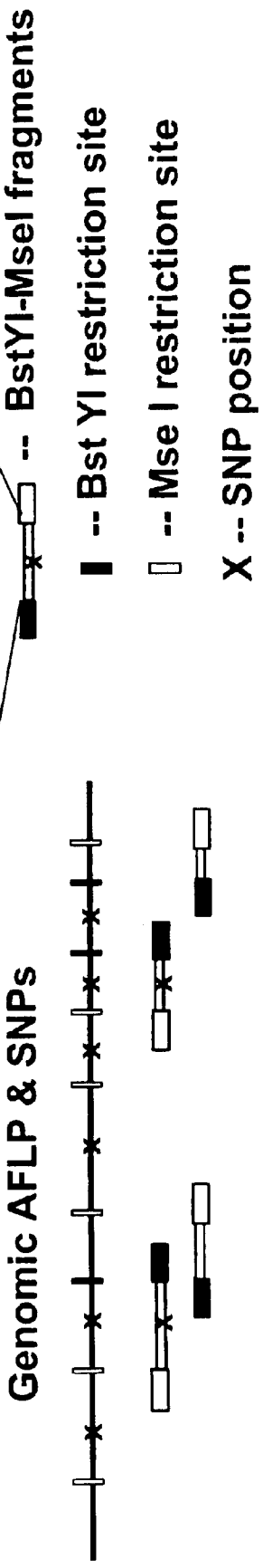
FIG. 2 shows a representation of the method of AFLP described in certain embodiments of the invention. Fragments are selectively binned into progressively smaller subsets by increasing the complexity of the primers used to amplify the fragments.

FIG. 2 illustrates the method by which AFLP fragments are generated by restriction enzyme digestion and selectively binned with progressively extend primers. For illustrative purposes, FIG. 3 shows the estimated number of mapped SNPs and AFLP fragments in selected bins amplified by primers extended by three nucleotides on the 3' ends of the primers.

AFLP

According to certain embodiments of the invention, amplification fragment length polymorphisms, or AFLPs are generated. Use of AFLPs has been described previously, e.g., in PCT publication WO 96/22388, and U.S. Pat. Nos. 5,874,215; and 6,045,994. In certain embodiments, AFLPs are generated from whole genomic DNA by first subjecting the DNA to digestion by at least one restriction enzyme. In certain embodiments, two restriction enzymes are used to digest the genomic DNA. In certain of these embodiments, the fragments generated from restriction enzyme digestion are ligated to adaptors. In certain embodiments, one uses the unique single stranded overhanging DNA remaining after restriction enzyme digestion to ligate an adaptor to the fragments. In certain embodiments, unique sequences may be used as sites for amplification primers specific to the adaptors. See FIG. 1.

In certain embodiments, primers are added to the fragments in order to amplify the fragments. In certain embodiments, the primers may be designed to complement the ligated adaptors employed in certain embodiments. In certain embodiments, the primers may be complementary to all or a portion of the sites of the restriction enzymes used to digest the DNA. In certain embodiments, these primers comprise a first primer pair, which further comprises a first primer and a second primer. In certain embodiments, the first primer of the first primer pair, and the second primer of the first primer pair comprise different sequences.

In certain embodiments of the invention, amplification of the fragments occurs in multiple reactions, generating the same AFLPs in multiple reaction containers.

Binning of AFLP Fragments

According to certain embodiments of the invention, extended primers are used for binning of, or differentiating between, different fragments. According to certain embodiments, the extended primers comprise sequences that are identical to the first primer and second primer used to generate the AFLPs, and further comprise a single nucleotide added to the 3' end of the primer oligonucleotides. In certain embodiments, the reaction containers are divided according to which extended primers are added to the reaction.

For example, one portion, or "bin," of the reaction containers may have an extended primer added which comprises the sequence of the first primer of the first primer pair, with an adenine ("A") nucleotide added to the 3' end of the primer. Another bin of reaction containers may have a primer comprising the sequence of the first primer of the first primer pair, but a guanidine ("G") nucleotide is added to the 3' end of the primer.

Thus, after amplification, the subset of amplified fragments that are amplified in the first bin should all have the nucleotide "A" immediately adjacent to the 3' end of the nucleotides of the first primer (as well as complementary sequences). Also, after amplification, the subset of amplified fragments that are amplified in the second bin should all have the nucleotide "G" immediately adjacent to the 3' end of the nucleotides of the first primer (as well as complementary sequences).

Similarly, one could use one, two, three, or four different extended second primers of the first primer set, which are binned by virtue of the extended nucleotide(s) (A, G, T, or C) at the 3' end of the second primer of the first primer pair. Thus, according to certain embodiments, one could use 16 different bins with the 16 different combinations of first and second extended primers. In such embodiments, the amplification in such bins should separate out fragments that have the 16 different possible combinations of single nucleotides immediately adjacent to the nucleotides of the restriction sites at either side of the fragment.

Successive rounds of subdivision of fragments into bins can be performed using further extended primers. For example, for a second subdivision, one would employ second extended primers that include the four possible extended nucleotides (A, G, C, or T) at the 3' end immediately adjacent to the first extended nucleotide of the first extended primer. Thus, if there were 16 different first extended primer pairs and 16 different second primer pairs, there would be 256 different bins with the 256 different combinations of two nucleotides adjacent to the restriction sites at either end of the fragments. By successive rounds of binning, one reduces the number of different fragments in each bin.

In certain embodiments, the extended primers are extended three times, and the last AFLP amplifications are performed with primers comprising the sequence of the first primer and second primer, and further comprise three nucleotides attached at the 3' end of the primers. See FIG. 2. In certain embodiments, the reaction containers are subdivided until there are over 1,000 bins.

Single Stranded Template Preparation

In certain embodiments, several copies of single-stranded AFLP are generated by asymmetric PCR. In certain embodiments, this occurs by adding a disproportionately higher amount of one amplification primer than the other amplification primer. The strand of DNA primer by the amplification of a higher amount continues to amplify after the complementary strand has run out of primer and no longer replicates. The strand that is generated is determined by which amplification primer is added in higher amounts.

In certain embodiments, asymmetric PCR occurs during the last rounds of AFLP amplification.

In certain embodiments, single stranded template may be generated by enzymatic degradation of one strand of double stranded nucleic acid. Such embodiments are typically performed by the exonuclease activity of an enzyme. In such embodiments one strand of the double stranded nucleic acid is made vulnerable to the nuclease activity, or the other strand is protected from the nuclease activity.

In certain embodiments, single-stranded template is generated by capturing one strand from a double stranded polynucleotide. In certain embodiments, the capturing is performed using biotin labeled nucleotides. In certain embodiments, the capturing is performed using an oligonucleotide complementary to one strand. In certain embodiments, the capturing is performed on a double-stranded polynucleotide which is then denatured and washed. In certain embodiments, one strand remains captured and the other strand is removed by the washing.

Detection

In certain embodiments, after the number of AFLPs in each reaction container has been reduced to a calculated number of AFLPs containing SNPs, the SNPs are detected. In certain embodiments single base extension is used to detect a nucleotide after AFLP. In certain embodiments, single base extension is used to detect a nucleotide on a single stranded template.

In certain embodiments, the particular nucleotide at an SNP may be detected using a fluorescent indicator. In certain embodiments, the fluorescent indicator can be a fluorescing dye connected to a quenching molecule by a specific oligonucleotide. These include, but are not limited to, 5'-nuclease fluorescent indicators and molecular beacons. Examples of such systems are described, e.g., in U.S. Pat. Nos. 5,538,848 and 5,723,591. In certain embodiments, one uses four indicators that can be distinguished from one another and each of the four indicators corresponds to a particular nucleotide (A, T, G, or C).

In certain embodiments, a minisequencing reaction is used to detect the SNP. In certain embodiments, the minisequencing reaction is performed under isothermal conditions.

Long Oligonucleotide Primers

Figure 4:
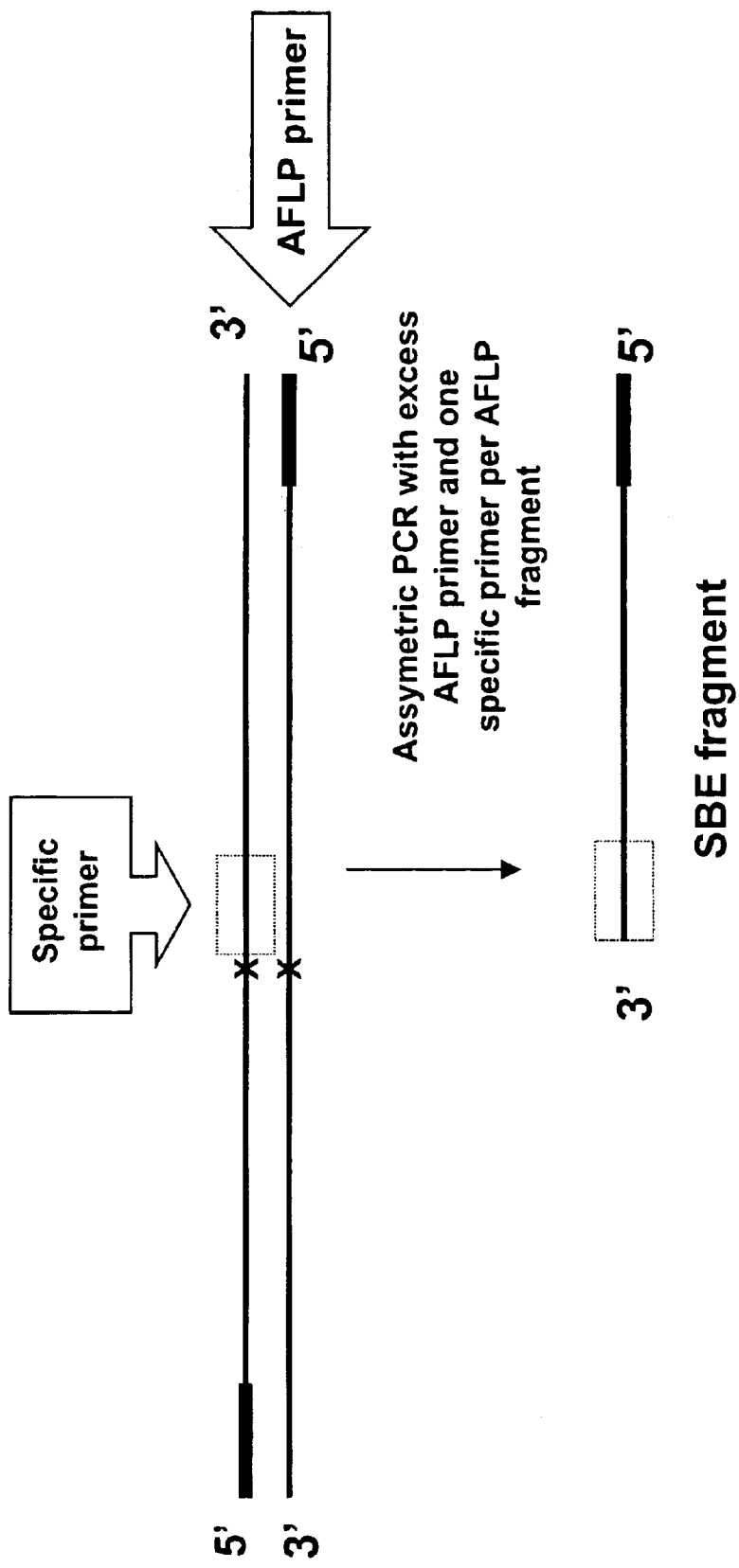
FIG. 4 illustrates the position of the primers used in asymmetric PCR to generate Long Oligonucleotide Primers for use in single base extension (SBE) sequencing reactions.

According to certain embodiments, AFLPs are generated as previously described. In certain embodiments, further amplification is performed with a portion of material of a bin, a primer from the first primer pair, and at least one SNP specific primer which comprises a sequence of an area immediately adjacent to an SNP. In certain embodiments, the at least one SNP specific primer which comprises a sequence of an area immediately adjacent to an SNP has the 5' end proximal to the SNP. See FIG. 4. An excess of the previously employed primer from the first primer pair is added to generate a long oligonucleotide primer of a known length, wherein the 3' end of the long oligonucleotide primer is proximal to the SNP. See FIG. 4. In certain embodiments, one can make multiple different long oligonucleotide primers that correspond to different SNPs within a given fragment or fragments within a bin. One can use different SNP specific primers that comprise a sequence of an area immediately adjacent to each different SNP. In these embodiments, amplification using the different SNP specific primers results in different long oligonucleotide primers that are specific for the different SNPs. Such long oligonucleotide primers will be of different length depending on the distance between the SNP and the end of the first primer (the nonextended primer).

In certain embodiments, one uses the long oligonucleotide primers in a minisequencing reaction to identify particular SNPs. According to certain embodiments, one performs a reaction with the different long oligonucleotide primers, a portion of the initial bin of AFLP fragments (prior to long oligonucleotide primer preparation), and sequence terminators. In certain embodiments, four different sequence terminators are used that each include a different indicator for each of the four nucleotides of the terminators (A, T, G, and C). According to certain embodiments, one tries to substantially remove or modify single nucleotides in the reaction so that they will not polymerize in a polymerase reaction. One carries out single base extension reactions using the sequence terminators to generate SNP containing sequences comprising nucleotides of the long oligonucleotide primer and an added labeled nucleotide, which corresponds to the SNP site. One can then separate the SNP containing sequences based on their size to differentiate between different SNP sites. One can also determine the specific nucleotides at each SNP site in view of the distinguishable indicator on the SNP containing sequence. In certain embodiments, the minisequencing reaction is performed isothermally.

Distinguishing fragments or long oligonucleotide primers by mobility may be accomplished by a variety of methods. In certain embodiments, single base extension primers are resolved by electrophoresis.

Unique Sequence Identifiers and Mobility Modifiers

Figure 5:
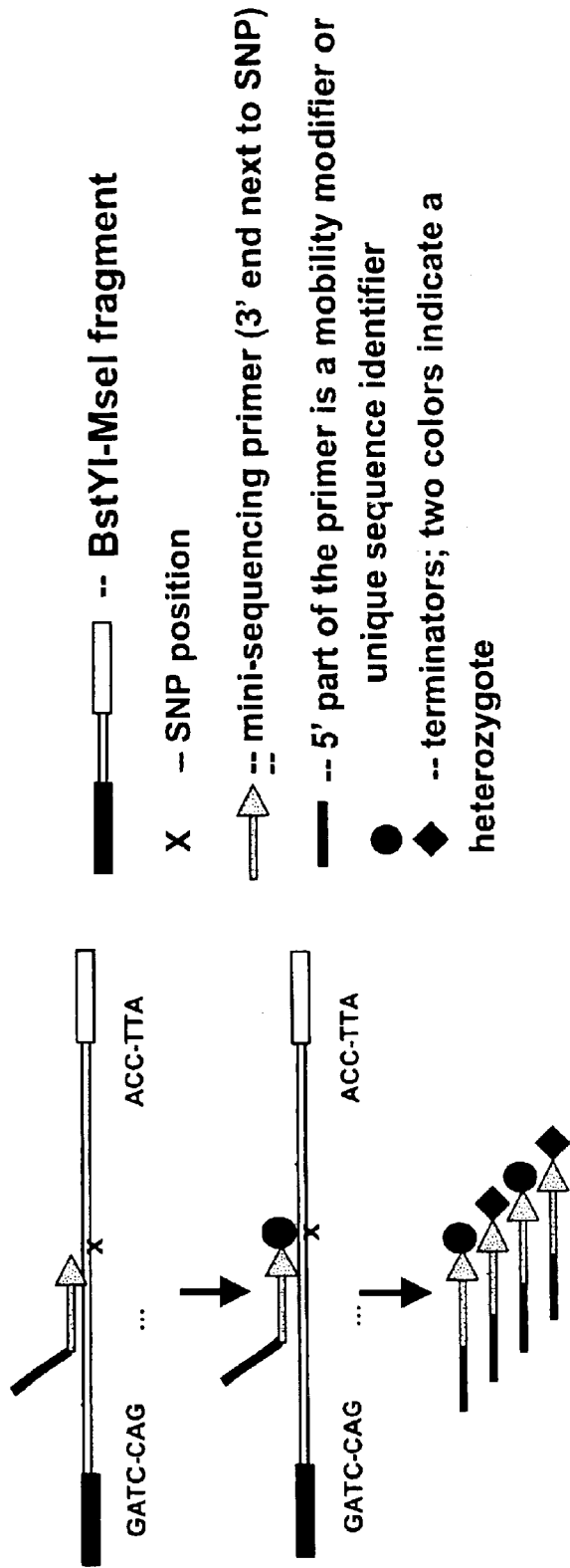
FIG. 5 illustrates the use of fragment specific sequencing primers for a single base extension sequencing reaction employing unique sequence identifiers or mobility modifiers.

In certain embodiments, amplification of AFLPs and asymmetric PCR to generate single-stranded DNA are performed as described. According to certain embodiments, one tries to substantially remove or modify single nucleotides in the reaction so that they will not polymerize in a polymerase reaction. In certain embodiments, primers comprising the sequence of an area immediately adjacent to an SNP are added to the reaction. These primers are designed so that the 3' end of the primer is proximal to the SNP. In certain embodiments, labeled sequence terminators are added to the reaction container, and minisequencing reactions are performed on the primers comprising the sequence of the area immediately adjacent to the SNP to obtain SNP containing sequences that comprise the primer and the added labeled nucleotide. In certain embodiments, a different label (indicator) is used for each different nucleotide terminator (A, C, G, or T). See FIG. 5. In certain embodiments, the minisequencing reaction is performed isothermally.

Distinguishing fragments or primers by mobility may be accomplished by a variety of methods. In certain embodiments, single base extension primers are resolved by electrophoresis.

In certain embodiments, the primers comprising the sequence of the area immediately adjacent to, but not including, the SNP further comprise a unique identifier sequence on the 5' end of the sequence of the area immediately adjacent to, but not including, the SNP. See FIG. 5. In certain embodiments, one uses multiple different unique identifier sequences corresponding to different SNP sites. In certain embodiments, the unique identifier sequences are complementary to different sequences on different locations on an array. One can then separate the SNP containing sequences based on their binding to the different locations on the array to differentiate between different SNP sites. One can also determine the specific nucleotides at each SNP site in view of the distinguishable indicator on the SNP containing sequence.

In certain embodiments, the primers comprising the sequence of the area immediately adjacent to the SNP further comprise a mobility modifier. In certain embodiments, one uses multiple different mobility modifiers for each different SNP site to be analyzed. One carries out single base extension reactions using the labeled sequence terminators to generate SNP containing sequences comprising nucleotides of primer with the mobility modifier and an added labeled nucleotide, which corresponds to the SNP site. One can then separate the SNP containing sequences based on the different mobilities for the different SNP sites. One can also determine the specific nucleotides at each SNP site in view of the distinguishable indicator on the SNP containing sequence.

In certain embodiments, each unique sequence identifier is complementary to a particular mobility-modifier comprising a tag complementary to the unique sequence identifier portion of the amplification product, and a tail for effecting a particular mobility in a mobility-dependent analysis technique, e.g., electrophoresis, see, e.g., U.S. patent application Ser. No. 09/522,640, filed Mar. 15, 1999.

Oligonucleotide Ligation Assay

In certain embodiments, SNPs are detected by an oligonucleotide ligation assay (OLA). OLA has been described, e.g., in U.S. Pat. No. 5,185,243. In certain embodiments, AFLPs are amplified and asymmetric PCR is performed to generate single-stranded DNA. In certain embodiments, primers comprising the sequence of an area immediately adjacent to a SNP are added to the reaction containers. Different primers comprising (i) the area immediately adjacent to the other side of the SNP and (ii) different possible nucleotides complementary to the SNP are added to the reaction containers. In certain embodiments, the different primers comprising the area immediately adjacent to the other side of the SNP and comprising different possible nucleotides complementary to the SNP, are distinguished by mobility modifiers, different lengths of the primer, or by different labels. Ligation reactions are performed and primers comprising the nucleotide complementary to the SNP are detected by the presence of ligation products.

In certain embodiments either or both primers can be designed to permit differentiation of different SNP sites within fragments. For example, one or both of the primers may include a sequence identifier and/or mobility modifier distinct for each SNP site, which permits one to differentiate between different SNP sites. The primer that includes the possible nucleotides complementary to the particular nucleotide at the SNP sites also may include an indicator specific for the particular SNP complementary nucleotide. Thus, one may also determine the particular nucleotide of each differentiated SNP site.

According to certain embodiments of the invention, a kit is provided. In certain embodiments, such a kit comprises a first pair of primers for the amplification of AFLPs. The first pair of primers comprise a first primer and a second primer. Such a kit further comprises extended primers, wherein the extended primers comprise a sequence identical to the primers used to generate the AFLPs, and further comprise a single nucleotide added to the 3' end of the primer oligonucleotide.

In certain embodiments, the kit further comprises several pairs of primers, wherein each pair of primers comprises sequences identical to the first primer and second primer used to generate the AFLPs, and further comprise one or more nucleotides added to the 3' end of the primer oligonucleotide, such that AFLPs amplified with successively longer primers may be subdivided into multiple bins.

In certain embodiments, the kit further comprises at least one primer which comprises a sequence of an area immediately adjacent to an SNP. In certain further embodiments, the at least one primer which comprises a sequence of an area immediately adjacent to an SNP further comprises a unique sequence identifier. In certain further embodiments, the at least one primer which comprises a sequence of an area immediately adjacent to an SNP further comprises a mobility modifier. In certain embodiments, the kit further comprises labeled sequence terminators.

According to certain embodiments, software is provided. In certain embodiments, this software identifies known SNPs from an electronic database, designs primers comprising sequence of an area immediately adjacent to a known SNP, calculates melting temperatures for the primers, and selects a primer based on the calculated melting temperature.

In certain embodiments, the software identifies sequences within a genome that begin with a certain first primer sequence and end with a certain second primer sequence. In certain embodiments, the software calculates the effect on the melting temperatures of particular salt concentrations used in a prospective buffer. In certain embodiments, the software eliminates from analysis SNPs that are 10 base pairs, or fewer than 10 base pairs, from a repeat sequence. In certain embodiments, the software uses the percent of double stranded sequence at an annealing temperature as a criteria for primer selection. In certain embodiments, the software determines whether there is a single location in a genome for an SNP. In certain embodiments, the software sorts selected primers by length, and adds an oligonucleotide at the end of the primer.

EXAMPLES

Example 1

A. Preparation of AFLP Template Mixture

Twelve different AFLP fragments of different lengths were obtained from Celera (Foster City, Calif.). The fragments were generated by digestion of rat genomic DNA with Bst YI and Mse I. The digestion products were ligated to oligonucleotide adaptors. The products were then amplified using the Ms000 and Bs000 primers (shown in Table 2). The products of those amplifications were then amplified with combinations of the primers shown in Table 4. Finally, the fragments were amplified with those primers identified in Table 1, the sequences of which are shown in Table 2. Lengths of the fragments differed from 50 base pairs to 435 base pairs. The 12 individual fragments were isolated and purified by Celera (Foster City, Calif.).

These 12 purified fragments were then mixed together. The mixture of these fragments was used as a model AFLP Template mixture. Table 1 shows the copy number and fragment length of each fragment in the mixture.

One (1) $\mu$l of the model AFLP mixture of the above AFLPs ($10^7$–$10^8$ copies of each) was amplified in a 100 $\mu$l PCR reaction using AmpliTaq Gold™ (available from Roche Molecular Systems, Inc.). The primers used in the reaction (Bs000 and Ms000) are designed to generally amplify the Mse I-Bst YI fragments with adaptors, and are defined in Table 2:

| | |
|---|---|
| 10X AmpliTaq Gold ™ buffer | 10 $\mu$l |
| 2.5 mM each dNTP | 8 $\mu$l |
| 25 mM MgCl$_2$ | 8 $\mu$l |
| AmpliTaq Gold ™ | 1 $\mu$l |
| Bs000 (primer) | 5 $\mu$l |
| Ms000 (primer) | 5 $\mu$l |
| AFLP Template mixture | 1 $\mu$l |
| Water | 62 $\mu$l |

This amplification reaction was thermally cycled for 15 cycles according to the following parameters:

| | |
|---|---|
| 95° C. | 15 seconds |
| 64° C. | 120 seconds |
| 75° C. | 120 seconds |

After amplification, 4 $\mu$l of the reaction product was treated with shrimp alkaline phosphatase (SAP) and Exonuclease I. The phosphatase removes the phosphate from free single nucleotides, which prevents them from polymerizing during a sequencing reaction. This step helps to prevent the sequencing reaction from elongating past the single nucleotide one intends to determine. The exonuclease destroys unpolymerized oligonucleotide that has not extended to completion. Both SAP and Exonuclease I are available from USB Corp. (Part Nos. 70092Z and 70073Z, respectively). The reaction was carried out as follows:

TABLE 1

| SAP (1 Unit/µl) | 2 µl |
|---|---|
| Exonuclease I (10 Unit/µl) | 0.2 µl |
| water | 6 µl |
| amplification product | 4 µl |

| Template Length in base pairs | Primer Used in Amplification | Copies in 10 µl (in a dilution) |
|---|---|---|
| 50 | bs42/ms44 | $8.7 \times 10^8$ |
| 96 | bs42/ms43 | $1.2 \times 10^9$ |
| 86 | bs44/ms43 | $1.8 \times 10^9$ |
| 130 | bs42/ms41 | $5.2 \times 10^8$ |
| 179 | bs22/ms43 | $2.1 \times 10^9$ |
| 184 | bs21/ms13 | $2.9 \times 10^8$ |
| 224 | bs22/ms21 | $1.5 \times 10^9$ |
| 271 | bs21/ms34 | $8.7 \times 10^8$ |
| 324 | bs42/ms33 | $1.1 \times 10^9$ |
| 344 | bs42/ms42 | $1.1 \times 10^9$ |
| 356 | bs24/ms42 | $8.8 \times 10^8$ |
| 435 | bs21/ms43 | $5.4 \times 10^8$ |

The mixture was reacted at 37° C. for 1 hour, followed by 75° C. for 15 minutes to obtain amplification product from the AFLP Template Mixture. The definition of one unit of Exonuclease I is the amount of enzyme which catalyzes the release of 10 nmole of acid-soluble nucleotide from denatured DNA in 30 minutes at 37° C. under standard conditions. The definition of one unit of SAP is the amount of enzyme which catalyzes the hydrolysis of 1 µmole of p-nitrophenyl phosphate per minute in glycine/NaOH buffer (pH 10.4) at 37° C.

B. Detection Primer Preparation

Random areas near the middle of each fragment were chosen. Primers which complement these areas were designed. These primers were synthesized. Each primer had 23 nucleotides complementary to the particular fragment, and three of the primers had a number of T's added to the 5' end of the primers as follows:

| 130 bp AFLP fragment | 0 T's |
|---|---|
| 179 bp AFLP fragment | 4 T's |
| 184 bp AFLP Fragment | 8 T's |
| 224 bp AFLP Fragment | 12 T's |

The identity of these primers is shown in Table 3.

C. Minisequencing by Single Base Pair Extension

A minisequencing reaction was performed for a "multiplex" experiment with all 4 primers as follows:

| Ready Mix | 5 µl |
|---|---|
| SAP Treated Amplification product from the AFLP Template Mixture (Example 1A) | 1 µl |
| Primers for the 130, 179, 184, and 224 bp Fragments (0 T's, 4 T's, 8 T's, and 12 T's) 1 µl each (5 µM) | 4 µl total |
| Water | 0 µl |

Ready Mix contains enzyme, sequencing terminators and buffers, and is available as part of the SNaPshot kit, Applied Biosystems, Part Nos. 4323154 and 4312163. Sequence terminators are fluorescently labeled such that each nucleotide has a different color label, distinguishing them during fluorescent detection during or after electrophoretic resolution.

Four separate "singleplex" minisequencing reactions were performed with each of the primers above in separate reactions as follows:

| Ready Mix | 5 µl |
|---|---|
| SAP Treated Amplification product from the AFLP Template Mixture (Example 1A) | 1 µl |
| Primer (0 T's, 4 T's, 8 T's, or 12 T's) (5 µM) | 1 µl |
| Water | 3 µl |

All the reactions were thermally cycled for 25 cycles using the parameters as follows:

| 96° C. | 10 seconds |
|---|---|
| 50° C. | 5 seconds |
| 60° C. | 30 seconds |

Each sample was then treated with 0.5 Units of SAP at 37° C. for 1 hour, then 72° C. for 15 minutes. All reactions were analyzed on an ABI Prism® 310.

Figure 6:
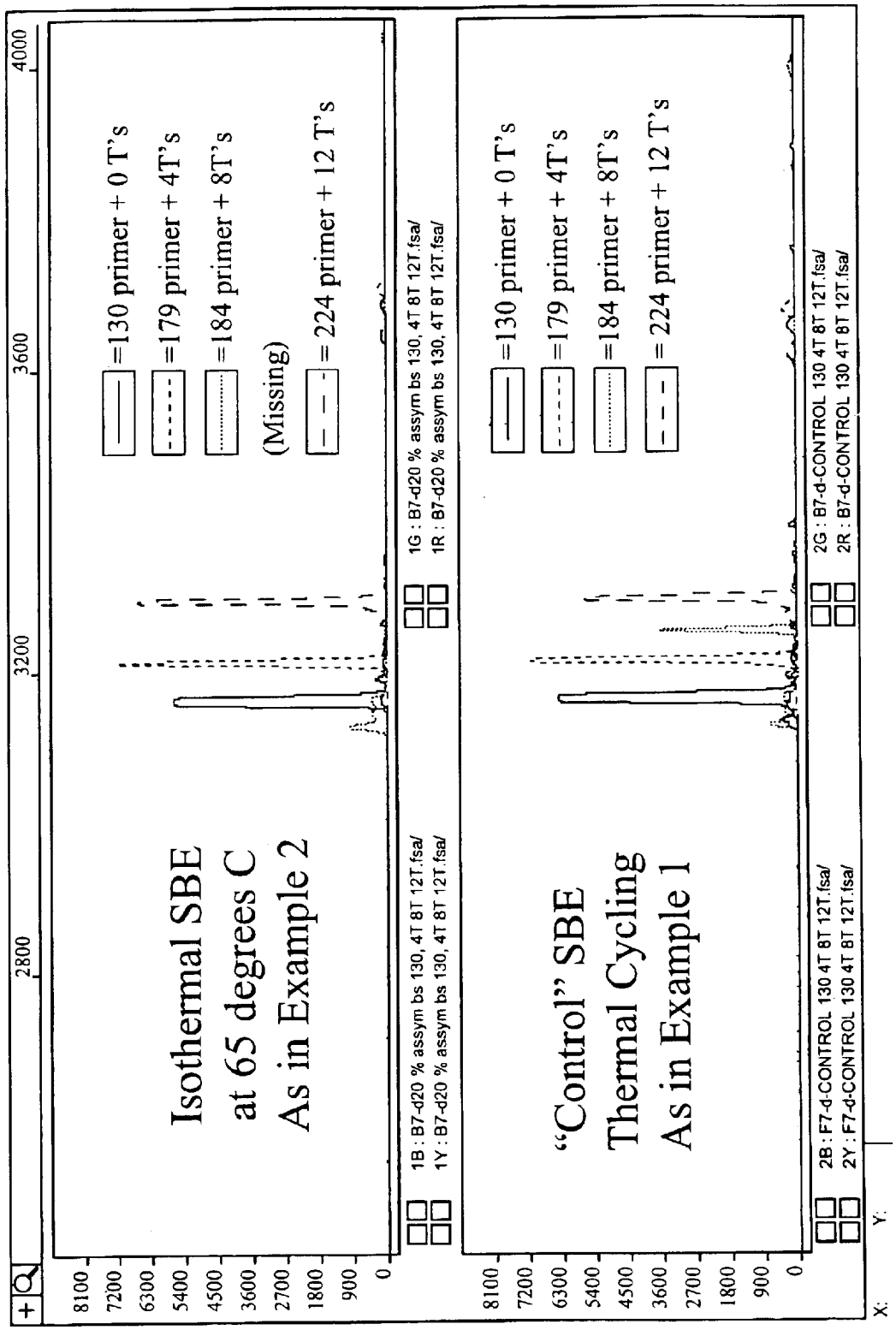
FIG. 6 shows the results of the multiplex sequence reactions used in Examples 1 and 2.

All reactions showed expected signals, indicating that multiplex single base extension minisequencing reactions are possible. The multiplex reaction results are shown in FIG. 6.

Example 2

A. Asymmetric Template Preparation

One (1) µl of the model AFLP mixture of the twelve AFLPs ($10^7$–$10^8$ copies of each) from Example 1 was amplified in a 100 µl PCR reaction using AmpliTaq Gold™ (available from Roche Molecular Systems, Inc.). The primers used in the reaction (Bs000 and Ms000) are designed to generally amplify the Mse I-Bst YI fragments with adaptors, and are defined in Table 2. Three separate reactions were performed to generate single stranded template, using three different concentrations of the Bs000 primer in reactions as follows:

| 10X AmpliTaq Gold ™ buffer | 10 µl |
|---|---|
| 2.5 mM each dNTP | 8 µl |
| 25 mM MgCl$_2$ | 8 µl |
| AmpliTaq Gold ™ | 1 µl |
| Bs000 (primer) (in 5 µM, 1 µM, and 0.1 µM concentrations) | 5 µl |
| Ms000 (primer) (5µM) | 5 µl |
| AFLP Template mixture | 1 µl |
| Water | 62 µl |

These reactions were thermally cycled for 15 cycles according to the following parameters:

| 95° C. | 15 seconds |
|---|---|
| 64° C. | 120 seconds |
| 75° C. | 120 seconds |

After amplification, 4 µl of the reaction products were treated with SAP in the following reaction:

| | |
|---|---|
| SAP (1 Unit/µl) | 2 µl |
| water | 6 µl |
| amplification product | 4 µl |

B. Minisequencing by Isothermal Single Base Pair Extension

Minisequencing was performed by using the primers for the 4 fragments (130 bp 0 T's, 179 bp 4 T's, 184 bp 8 T's, and 224 bp 12 T's) of Example 1. The minisequencing reaction was performed for the "multiplex" experiment with all 4 primers as follows:

| | |
|---|---|
| Ready Mix | 5 µl |
| SAP Treated Amplification product from the AFLP Template Mixture (Example 2A) | 1 µl |
| Primers (5 µM), 1 µl each of (130 0 T's, 179 4T's, 184 8 T's, and 224 12 T's) | 4 µl total |
| Water | 0 µl |

Four "singleplex" minisequencing reactions were performed with each of the primers above in separate reactions as follows:

| | |
|---|---|
| Ready Mix | 5 µl |
| SAP Treated Amplification product from the AFLP Template Mixture (Example 2A) | 1 µl |
| Primers (5 µM), 1 µl each of (130 0 T's, 179 4 T's, 184 8 T's, or 224 12 T's) | 1 µl |
| Water | 3 µl |

All the reactions were incubated at 65° C. for 1 hour, without cycling. Each sample was then treated with 0.5 Units of SAP at 37° C. for 1 hour, then 72° C. for 15 minutes. All reactions were analyzed on an ABI Prism® 310.

The results indicated that the 1:5 ratio of Bs000/Ms000 primer ratio gave the strongest signal, while smaller ratios (1:10 and 1:100) gave less signal. The symmetric PCR (using a 1:1 ratio of primer) gave almost no signal. Data not shown. One of the multiplex reactions is shown in FIG. 6. The weak "green" signal is likely the result of the specific primer sequence used in that reaction.

Example 3

A. AFLP Template Mixture Preparation

One (1) µl of the model AFLP mixture of the 12 AFLPs ($10^7$–$10^8$ copies of each) from Example 1 was amplified in a 100 µl PCR reaction using AmpliTaq Gold™ (available from Roche Molecular Systems, Inc.). The primers used in the reaction (Bs000 and Ms000) are designed to generally amplify the Mse I-Bst YI fragments with adaptors, and are defined in Table 2. The amplification was performed with the following components:

| | |
|---|---|
| 10X AmpliTaq Gold ™ buffer | 10 µl |
| 2.5 mM each dNTP | 8 µl |
| 25 mM MgCl$_2$ | 8 µl |

-continued

| | |
|---|---|
| AmpliTaq Gold ™ | 1 µl |
| Bs000 (primer) | 5 µl |
| Ms000 (primer) | 5 µl |
| AFLP Template mixture | 1 µl |
| Water | 62 µl |

This reaction was thermally cycled for 40 cycles according to the following parameters:

| | |
|---|---|
| 95° C. | 15 seconds |
| 64° C. | 120 seconds |
| 75° C. | 120 seconds |

After amplification, 4 µl of the reaction product was treated with SAP and Exonuclease I. The reaction was as follows:

| | |
|---|---|
| SAP (1 Unit/µl) | 2 µl |
| Exonuclease I (10 Unit/µl) | 0.2 µl |
| water | 6 µl |
| amplification product | 4 µl |

The mixture was reacted at 37° C. for 1 hour, followed by 75° C. for 15 minutes.

B. Long Oligonucleotide Primer Preparation by Asymmetric PCR

Figure 7:
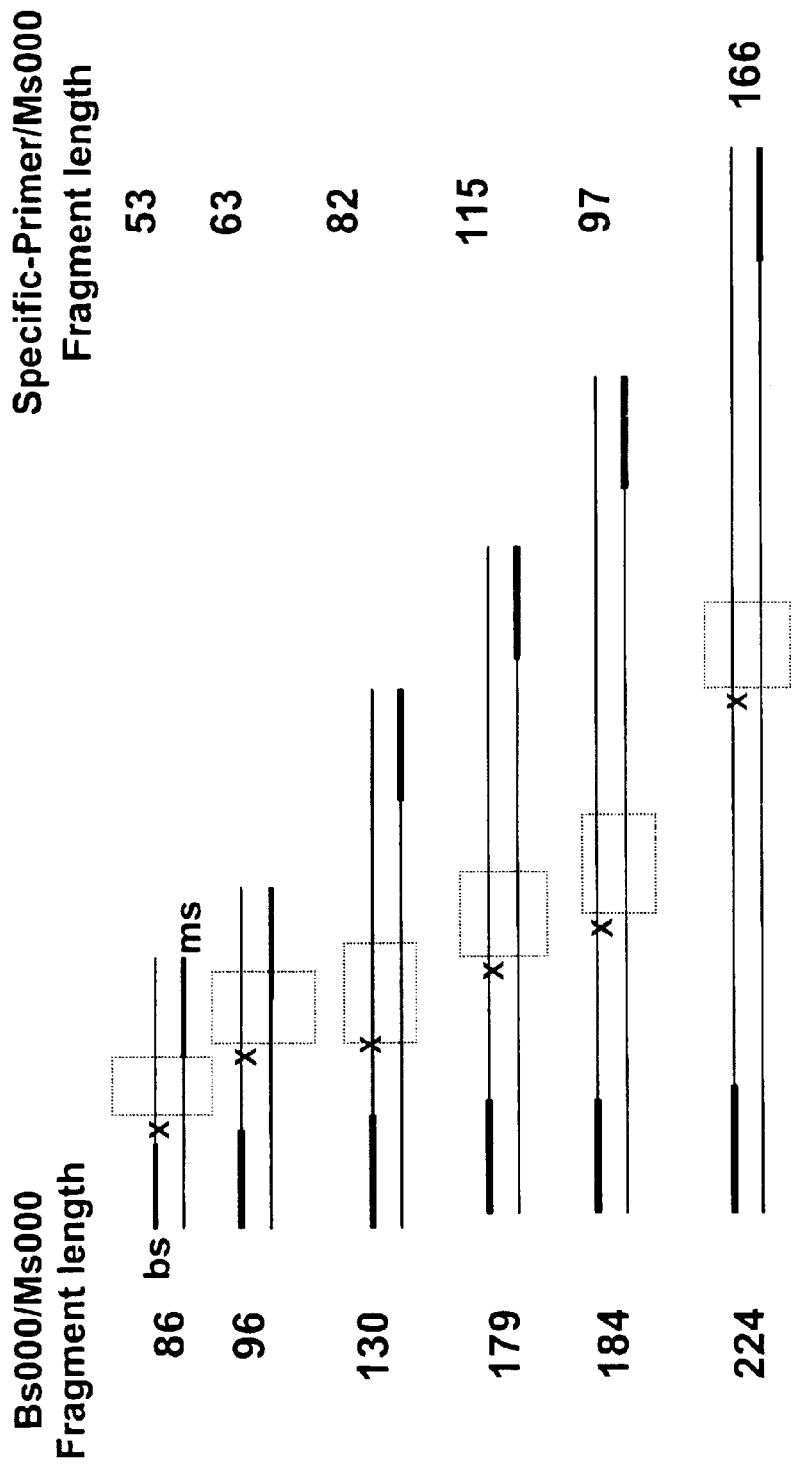
FIG. 7 illustrates the positions of the specific primers used in Examples 3 and 5 relative to the total fragment.

Areas adjacent to each of the 10 selected nucleotides in 10 of the twelve fragments were chosen, and primers were designed complementary to these areas. The primers were synthesized. The sequence of each of the primers is shown in Table 3. The fragments corresponding to the lengths 50 base pairs and 435 base pairs fragments were not synthesized. FIG. 7 shows the relative placement of 6 of the primers of Table 3 on the corresponding fragment adjacent to the "model SNP" site (x). The 10 primers were mixed together in a final a concentration of 0.5 µM for each primer. One (1) µl of this mixture, corresponding to 0.5 pmole of each primer, was used for asymmetric PCR in the following reaction:

| | |
|---|---|
| 10x AmpliTaq Gold ™ buffer | 2 µl |
| 2.5 mM each dNTP | 1.6 µl |
| 25 mM MgCl$_2$ | 1.6 µl |
| AmpliTaq Gold ™ | 0.2 µl |
| Primer mixture | 1 µl |
| Ms000 (in a 5 µM concentration) | 3 µl |
| AFLP Template mixture | 0.2 µl |
| water | 10.4 µl |

This reaction was thermally cycled for 40 cycles with the following parameters:

| | |
|---|---|
| 95° C. | 15 seconds |
| 64° | 120 seconds |
| 75° | 120 seconds |

Twelve μl of the resulting amplification product were used in the following reaction:

| | |
|---|---|
| SAP (1 Unit/μl) | 12 μl |
| Water | 12.6 μl |
| Amplification Product | 12 μl |

The mixture was reacted at 37° C. for 1 hour, followed by 75° C. for 15 minutes.

C. Minisequencing by Single Base Extension

Minisequencing reactions were carried out as follows:

| | |
|---|---|
| Ready Mix | 5 μl |
| SAP Treated Amplification product from the AFLP Template Mixture (Example 3A) | 2.5 μl |
| Long Oligonucleotide Primer Product (Example 3B) | 2.5 μl |

The reaction was subjected to thermal cycling using the following parameters for 25 cycles:

| | |
|---|---|
| 96° C. | 10 seconds |
| 50° C. | 5 seconds |
| 60° C. | 30 seconds |

Figure 8:
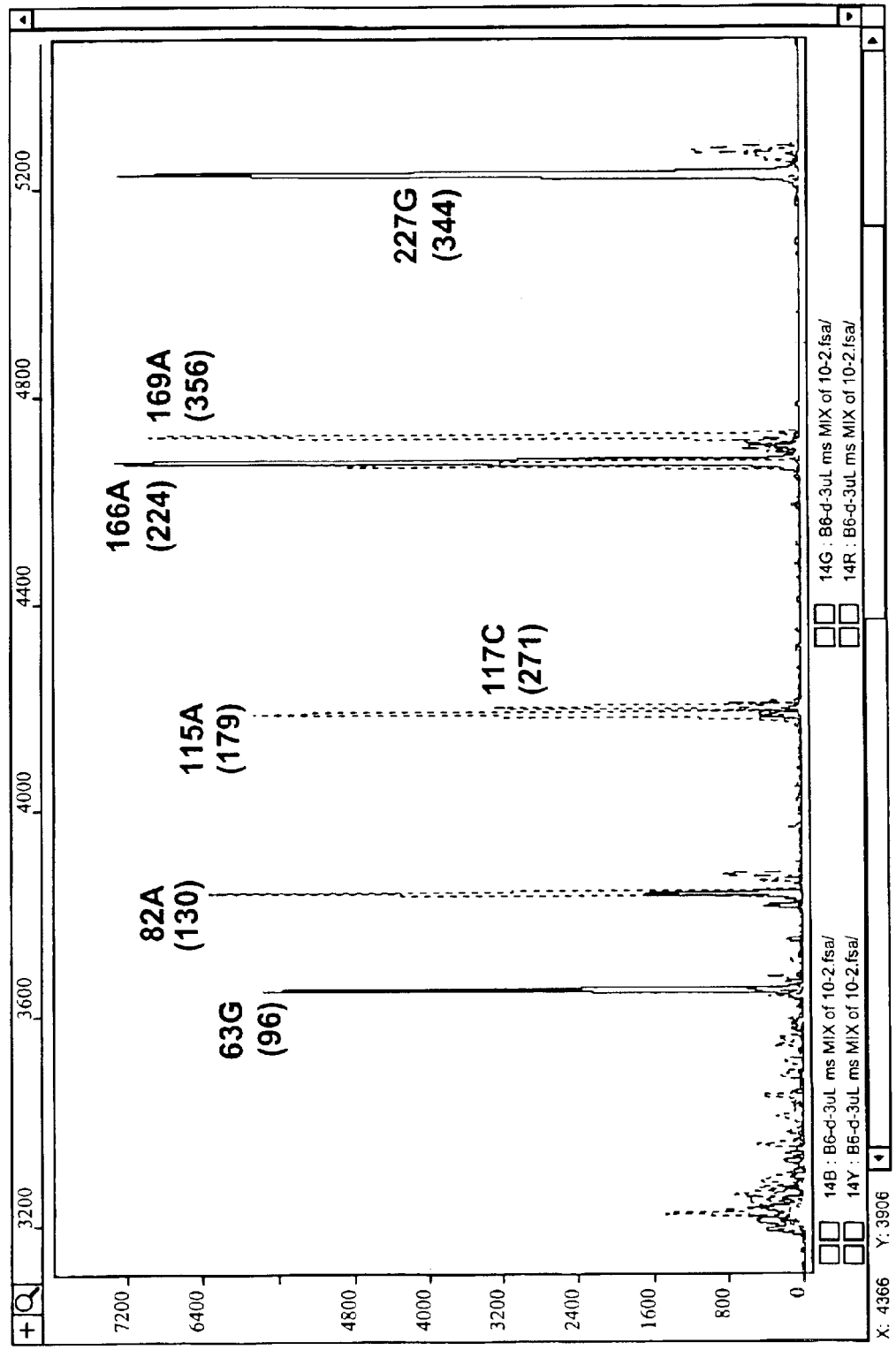
FIG. 8 shows the results of Example 3. Seven single nucleotide sequences are correctly detected in a multiplex reaction.

SAP (0.75 Units) was added to the reaction after cycling was complete, and incubated for 1 hour at 37° C. The reaction was then subjected to 75° C. for 15 minutes and analyzed on the ABI Prism® 310 Genetic Analyzer (Applied Biosystems). The results are shown in FIG. 8.

Example 4

A. Long Oligonucleotide Primer Preparation

Two primers were designed and synthesized that differed in melting temperature. The one named 60F anneals at 60° C., while 65F anneals at 65° C. Both primers comprise the same sequence, except the 65F primer includes 2 additional nucleotides at the 5' end compared to the 60F primer. Sequences of 60F and 65F are shown in Table 2. In two different separate reactions, 1 pmole of either 60F or 65F was combined with 15 pmole of Ms000 in a 20 μl amplification reaction. The reactions were composed as follows:

| | |
|---|---|
| 10X AmpliTaq Gold ™ buffer | 2 μl |
| 2.5 mM each dNTP | 1.6 μl |
| 25 mM MgCl$_2$ | 1.6 μl |
| AmpliTaq Gold ™ | 0.2 μl |
| 60F or 65F primer (1 μM) | 1 μl |
| Ms000 (in a 5 μM concentration) | 3 μl |
| AFLP Template mixture | 0.2 μl |
| water | 10.4 μl |

The reactions were thermally cycled for 40 cycles according to the following parameters:

| | |
|---|---|
| 95° C. | 15 seconds |
| 64° C. | 120 seconds |
| 75° C. | 120 seconds |

The resultant amplification products was subjected to SAP treatment as follows:

| | |
|---|---|
| SAP (1 Unit/μl) | 2 μl |
| water | 6.2 μl |
| Amplification product | 4 μl |

The reactions occurred at 37° C. for 1 hour, followed by 75° C. for 15 minutes.

B. Asymmetric PCR

The products from Example 4A were used as Long Oligonucleotide Primers in asymmetric PCR as follows:

| | |
|---|---|
| 10X AmpliTaq Gold ™ buffer | 2 μl |
| 2.5 mM each dNTP | 1.6 μl |
| 25 mM MgCl$_2$ | 1.6 μl |
| AmpliTaq Gold ™ | 0.2 μl |
| Long Oligonucleotide Primer Product | 1 μl |
| Bs000 (in a 5 μM concentration) | 3 μl |
| AFLP Template mixture | 0.2 μl |
| Water | 10.4 μl |

The reactions were thermally cycled for 40 cycles according to the following parameters:

| | |
|---|---|
| 95° C. | 15 seconds |
| 64° C. | 120 seconds |
| 75° C. | 120 seconds |

The resultant amplification products were subjected to SAP treatment as follows:

| | |
|---|---|
| SAP (1 Unit/μl) | 2 μl |
| water | 6.2 μl |
| Asymmetric Amplification product | 4 μl |

The mixtures were reacted at 37° C. for 1 hour, followed by 75° C. for 15 minutes. The Asymmetric Amplification products were then used as Single-Stranded Template.

C. Minisequencing by Single Base Extension

A minisequencing reaction was performed as follows:

| | |
|---|---|
| Ready Mix | 5 μl |
| Long Oligonucleotide Primer Product (Example 4A) | 2.5 μl |
| SAP treated Asymmetric Amplification Product (Example 4B) | 2.5 μl |

Thermal cycling occurred for 75 cycles as follows:

| | |
|---|---|
| 96° C. | 10 seconds |
| 70° C. | 30 seconds |

Figure 9:
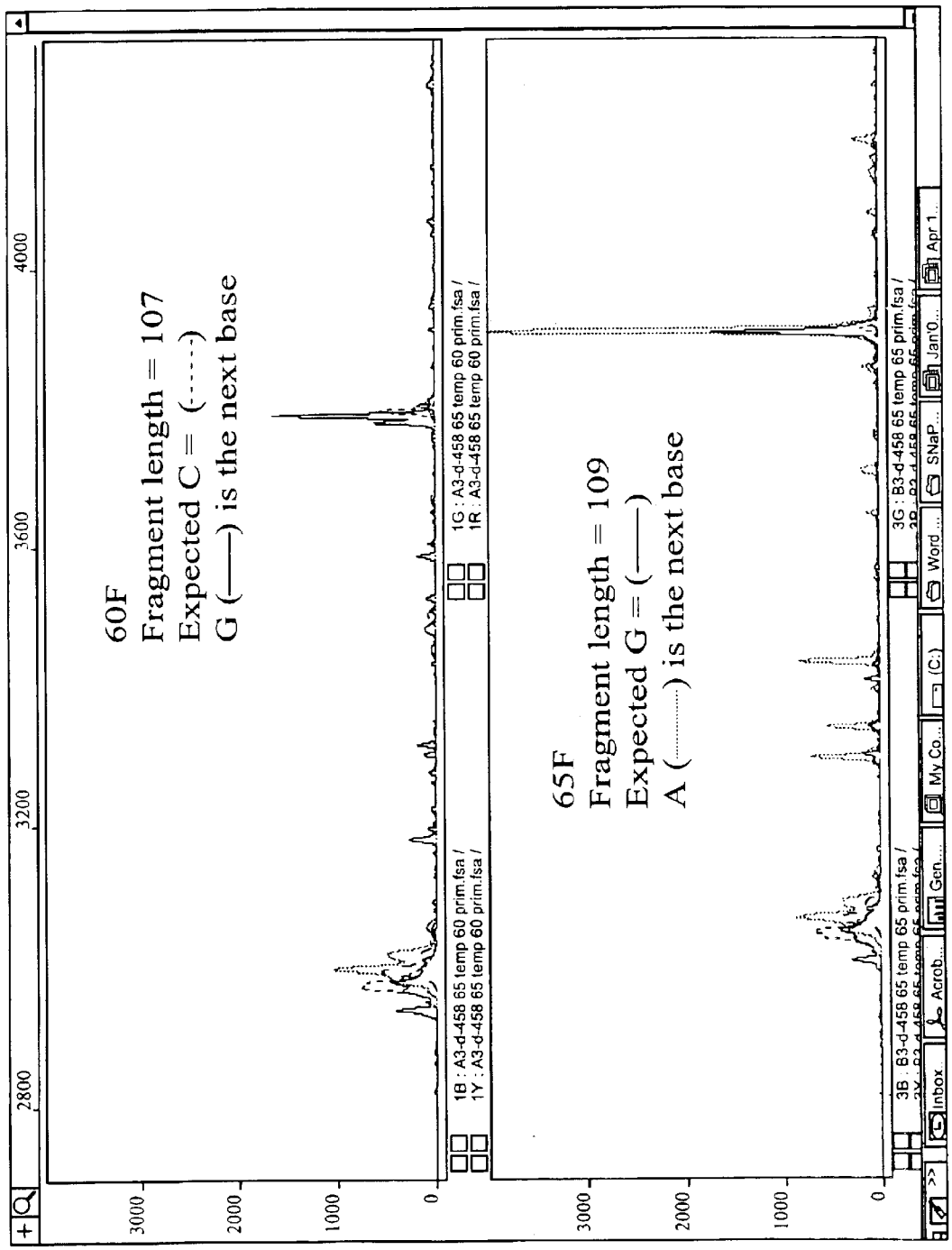
FIG. 9 shows the results of Example 4. Correct identification of a single nucleotide sequence is shown for primers with Tm's of 60° C. and 65° C.

Both the 60F and 65F primer resulted in the correct signals for the known nucleotides detected. The signals appeared at the correct length. See FIG. 9. The results demonstrate that primers designed with both 60° C. and 65° C. annealing temperatures work for Long Oligonucleotide Primer preparation under these conditions.

Example 5

A. AFLP Template Mixture Preparation

A subset AFLP mixture, amplified with primers designated Bs244 and Ms111 (shown in Table 2), was obtained from Celera (Foster City, Calif.). These primers included the Bs000 primer sequence with CTT added on the 3' end, and the Ms000 primer sequence with AAA added on the 3' end. These primers were used in a reaction as follows:

| | |
|---|---|
| 10X AmpliTaq Gold ™ buffer | 10 µl |
| 2.5 mM each dNTP | 8 µl |
| 25 mM MgCl₂ | 8 µl |
| AmpliTaq Gold ™ | 1 µl |
| Primer Bs244 | 5 µl |
| Primer Ms111 | 5 µl |
| Subset AFLP mixture | 20 µl |
| Water | 43 µl |

Thermal cycling occurred for 40 cycles with the following parameters:

| | |
|---|---|
| 95° C. | 15 seconds |
| 75° C. | 240 seconds |

Half of the resultant product was added to 11 µl of SAP at 1 Unit/µl, without dilution in water. The mixture was reacted at 37° C. for 1 hour, followed by 75° C. for 15 minutes.

B. Long Oligonucleotide Primer Preparation

Long Oligonucleotide Primers were generated in separate reactions using 10 fragment specific primers as shown in Table 5. The separate reactions mixtures were prepared as follows:

| | |
|---|---|
| 10X AmpliTaq Gold ™ buffer | 10 µl |
| 2.5 mM each dNTP | 8 µl |
| 25 mM MgCl₂ | 8 µl |
| AmpliTaq Gold ™ | 1 µl |
| One of the 10 Specific primers (5 µM) | 1 µl |
| Ms000 (5 µM) | 5 µl |
| AFLP Template mixture | 1 µl |
| Water | 66 µl |

Thermal cycling occurred for 40 cycles with the following parameters:

| | |
|---|---|
| 95° C. | 15 seconds |
| 64° C. | 240 seconds |
| 75° C. | 240 seconds |

The entire product of each amplification reaction was added to separate containers with 22 µl SAP at 1 Unit/µl without dilution in water. The mixtures were reacted at 37° C. for 1 hour, followed by 75° C. for 15 minutes.

C. Minisequencing by Single Base Extension

A minisequencing reaction was performed as follows for each of the preceding Long Oligonucleotide Primer products:

| | |
|---|---|
| Ready Mix | 5 µl |
| Long Oligonucleotide Primer product (Example 5B) | 2.5 µl |
| SAP Treated Amplification product from the AFLP Template Mixture (Example 5A) | 2.5 µl |

The reactions were thermally cycled for 75 cycles with the following parameters:

| | |
|---|---|
| 96° C. | 15 seconds |
| 70° C. | 120 seconds |

Figure 10:
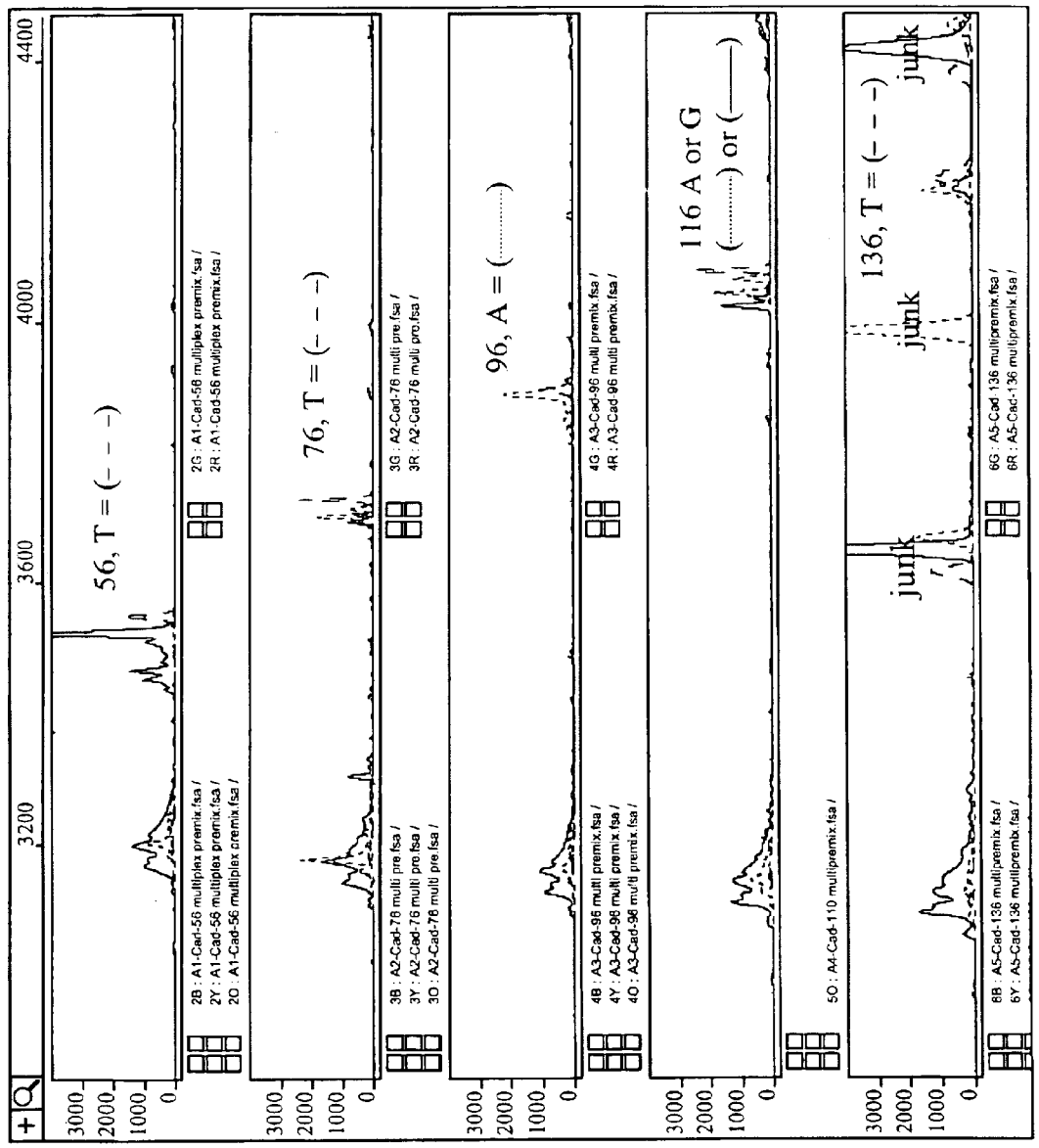
FIG. 10 shows the results of Example 5. Five of the specific primers demonstrated a nucleotide sequence at the proper site.

Signal was generated for each of the ten reactions when analyzed on an ABI Prism® 310 Genetic Analyzer. FIG. 10 shows the results of 5 of the 10 "singleplex" reactions. The results indicate that all the primers are capable of single base extension sequencing.

TABLE 2

| Primer | Sequence | SEQ ID NO. |
|---|---|---|
| Ms000 | GCG ACG ATG AGT CCT GAG TAA | 1 |
| Bs000 | CTC GTA GAC TGC GTA CCG ATC | 2 |
| Ms13 | GCG ACG ATG AGT CCT GAG TAA AG | 3 |
| Ms21 | GCG ACG ATG AGT CCT GAG TAA CA | 4 |
| Ms33 | GCG ACG ATG AGT CCT GAG TAA GG | 5 |
| Ms34 | GCG ACG ATG AGT CCT GAG TAA GT | 6 |
| Ms41 | GCG ACG ATG AGT CCT GAG TAA TA | 7 |
| Ms42 | GCG ACG ATG AGT CCT GAG TAA TC | 8 |
| Ms43 | GCG ACG ATG AGT CCT GAG TAA TG | 9 |
| Ms44 | GCG ACG ATG AGT CCT GAG TAA TT | 10 |
| Bs21 | CTC GTA GAC TGC GTA CCG ATC CA | 11 |
| Bs22 | CTC GTA GAC TGC GTA CCG ATC CC | 12 |
| Bs24 | CTC GTA GAC TGC GTA CCG ATC CT | 13 |
| Bs42 | CTC GTA GAC TGC GTA CCG ATC TC | 14 |
| Bs44 | CTC GTA GAC TGC GTA CCG ATC TT | 15 |
| Ms111 | GCG ACG ATG AGT CCT GAG TAA AAA | 16 |
| Bs244 | CTC GTA GAC TGC GTA CCG ATC CTT | 17 |
| 60F | ACT GTT GGA CAC ACA GGA G | 18 |
| 65F | GCA CTG TTG GAC ACA CAG GAG | 19 |

TABLE 3

| Primer | Sequence | SEQ ID NO. |
|---|---|---|
| 130 + 0 T's | CTG TCT CAT TCT TGG GTT TTC CT | 20 |
| 179 + 4 T's | TTT TGT AGC TCA TGG TGG AAC AAA TGG | 21 |

TABLE 3-continued

| Primer Sequence | | SEQ ID NO. |
|---|---|---|
| 184 + 8 T's | TTT TTT TTC TCT GAA GAT TTA TTA GAC GTT G | 22 |
| 224 + 12 T's | TTT TTT TTT TTT GGT ATC CCT TCG AAG GTT GCC TG | 23 |
| 86 | GAA TTG TTC TAT AAG GGC ATC CG | 24 |
| 96 | CCT GAC CCC TCT CCT TCA TAA AT | 25 |
| 130 | CTG TCT CAT TCT TGG GTT TTC CT | 26 |
| 179 | AGA ATG ACC TTC TTG GTC ATC CA | 27 |
| 184 | CTC TGA AGA TTT ATT AGA CGT TG | 28 |
| 224 | GGT ATC CCT TCG AAG TTG CCT G | 29 |
| 271 | CAT GGG TAT ATA GCC ATG TCC CT | 30 |
| 324 | GCC TTT GCT ACA CTG GCA CTC AC | 31 |
| 344 | TAA CTA CAA GGG ACA GGT GCT GA | 32 |
| 356 | CAT GAG GAC AAA TAT CAT TCT GA | 33 |

TABLE 4

| Fragment Lengths in bp | Primers Used | Sequence | SEQ ID NO. |
|---|---|---|---|
| 50, 86, 96, 130, 344 | bs4 | CTC GTA GAC TGC GTA CCG ATC T | 34 |
|  | ms4 | GCG ACG ATG AGT CCT GAG TAA T | 35 |
| 179, 356, 435 | bs2 | CTC GTA GAC TGC GTA CCG ATC C | 36 |
|  | ms4 | GCG ACG ATG AGT CCT GAG TAA T | 35 |
| 184 | bs2 | CTC GTA GAC TGC GTA CCG ATC C | 36 |
|  | ms1 | GCG ACG ATG AGT CCT GAG TAA A | 37 |
| 224 | bs2 | CTC GTA GAC TGC GTA CCG ATC C | 36 |
|  | ms2 | GCG ACG ATG AGT CCT GAG TAA C | 38 |
| 271 | bs2 | CTC GTA GAC TGC GTA CCG ATC C | 36 |
|  | ms3 | GCG ACG ATG AGT CCT GAG TAA G | 39 |
| 324 | bs4 | CTC GTA GAC TGC GTA CCG ATC T | 34 |
|  | ms3 | GCG ACG ATG AGT CCT GAG TAA G | 39 |

TABLE 5

| Total Fragment Length in bp | Length of SBE Primer in bp | Sequence | SEQ ID NO. |
|---|---|---|---|
| 160 | 56 | ACA TCC TTT CCA GCA TC | 40 |
| 182 | 76 | TCA GTC TCC ACA TTT GC | 41 |
| 160 | 96 | TAC ACT CCC ACC AAC A | 42 |
| 242 | 116 | CCT GCA GAT TTT GAT TCG | 43 |
| 364 | 136 | GTG TTA GCC AGG ATG G | 44 |
| 239 | 156 | GTG CTT CTA AGT ATA TGT GTA CT | 45 |
| 305 | 176 | GGG AGG GAG GTA TTC TAG | 46 |
| 459 | 196 | TCA TCA GAA TGA CTT AGC AG | 47 |
| 292 | 216 | CTG AGA TTT GAT CTC TTC TTC A | 48 |
| 284 | 235 | ATG CAA GAA ACC TTC AGG | 49 |

---

What is claimed is:

1. A method for identifying at least one target nucleotide within a target sequence comprising:

generating multiple fragments of the target sequence by digesting the target sequence with at least one restriction enzyme;

amplifying the multiple fragments using a first set of primers to generate multiple amplified fragments, wherein the first set of primers comprises a first primer and a second primer;

amplifying at least one subset of the multiple amplified fragments to generate at least one amplified subset of the multiple amplified fragments using a first set of extended primers, wherein the first set of extended primers comprises a first extended primer which comprises the sequence of the first primer and one additional nucleotide on the 3' end and a second extended primer which comprises the sequence of the second primer and one additional nucleotide on the 3' end;

amplifying the at least one subset of the multiple amplified fragments to generate at least one second subset of amplified fragments using a second set of extended primers, wherein the second set of extended primers comprises a third extended primer which comprises the sequence of the first extended primer and one additional nucleotide on the 3' end and a fourth extended primer which comprises the sequence of the second extended primer and one additional nucleotide on the 3' end; and identifying the at least one target nucleotide within a target sequence by identifying the at least one target nucleotide in at least one of the amplified subsets of the multiple amplified fragments.

2. The method according to claim 1, further comprising amplifying the at least one second subset of the multiple amplified fragments to generate at least one third subset of amplified fragments using a third set of extended primers, wherein the third set of extended primers comprises a fifth extended primer which comprises the sequence of the third extended primer and one additional nucleotide on the 3' end and a sixth extended primer which comprises the sequence of the fourth extended primer and one additional nucleotide on the 3' end.

3. The method of claim 1, further comprising ligating an adaptor to each end of the multiple fragments of the target sequence after the generating the multiple fragments of the target sequence and before the amplifying the multiple fragments, and wherein the first primer comprises a sequence complementary to the adaptor on one end of the multiple fragments of the target sequence and the second primer comprises a sequence complementary to the adaptor on the other end of the multiple fragments of the target sequence.

4. The method according to claim 1, further comprising asymmetrically amplifying the at least one amplified subset of the multiple amplified fragments to generate single-stranded template prior to the identifying the at least one target nucleotide within a target sequence.

5. The method according to claim 4, wherein the asymmetrically amplifying comprises amplifying with a primer comprising the sequence of one of the primers of the first set of primers, and at least one primer which comprises a sequence corresponding to an area immediately adjacent to a nucleotide to be identified;

wherein there is an excess of the primer comprising the sequence of one of the primers of the first set of primers compared to the at least one primer which comprises a sequence corresponding to an area immediately adjacent to a nucleotide to be identified;

to generate a long oligonucleotide primer of a known length, wherein the 3' end of the long primer is immediately adjacent to the nucleotide to be identified.

6. The method of claim 5, further comprising performing a single base extension reaction using the long oligonucleotide primer and sequence terminators having an indicator specific for the specific nucleotide of the sequence terminator, to generate a single base extension product; and identifying nucleotide to be identified.

7. The method according to claim 6, further comprising resolving the single base extension product according to the length of the long oligonucleotide primer.

8. The method according to claim 6, further comprising attaching a mobility modifier to the single base extension product and resolving the single base extension product by its mobility.

9. The method according to claim 6, wherein the single base extension reaction is performed isothermally.

10. A kit for the amplification of amplified fragment length polymorphisms comprising:

a first set of primers comprising a first primer and a second primer used to generate amplified fragment length polymorphisms;

a first set of extended primers comprising a third extended primer which comprises the sequence of the first primer and one additional nucleotide on the 3' end and a fourth extended primer which comprises the sequence of the second primer and one additional nucleotide on the 3' end; and a second set of extended primers comprising a fifth extended primer which comprises the sequence of the third extended primer and one additional nucleotide on the 3' end and a sixth extended primer which comprises the sequence of the fourth extended primer and one additional nucleotide on the 3' end.

11. A method for identifying a nucleotide at a SNP site comprising:

digesting genomic DNA with two restriction enzymes to generate multiple fragments of a target sequence;

ligating an adaptor to each end of the multiple fragments of the target sequence;

amplifying the multiple fragments to generate multiple amplified fragments using a first set of primers, wherein the first set of primers comprises a first primer and a second primer, wherein the first primer comprises a sequence complementary to the adaptor on one end of the multiple fragments of the target sequence and the second primer comprises a sequence complementary to the adaptor on the other end of the multiple fragments of the target sequence;

adding a first set of extended primers, wherein the first set of extended primers comprises a first extended primer which comprises the sequence of the first primer and one additional nucleotide on the 3' end and a second extended primer which comprises the sequence of the second primer and one additional nucleotide on the 3' end;

amplifying a subset of the multiple amplified fragments using the first set of extended primers to generate a first amplified subset of the multiple amplified fragments;

adding a second set of extended primers, wherein the second set of extended primers comprises a third extended primer which comprises the sequence of the first extended primer and one additional nucleotide on the 3' end and a fourth extended primer which comprises the sequence of the second extended primer and one additional nucleotide on the 3' end;

amplifying a second subset of the multiple amplified fragments employing the second set of extended primers to generate a second amplified subset of the multiple amplified fragments;

performing an asymmetric amplification of the second amplified subset of the multiple amplified fragments to generate multiple single stranded fragments;

performing a single base extension reaction using at least one of the multiple single stranded fragments, a single base extension primer, and sequence terminators having an indicator specific for the specific nucleotide of the sequence terminator, wherein the single base extension primer comprises (i) at its 3' end a sequence complementary to nucleotides immediately adjacent to the SNP site and (ii) a unique sequence identifier, to obtain a single base extension product; and identifying the nucleotide at the SNP site from the specific indicator.

* * * * *